United States Patent [19]

Chan

[11] Patent Number: 4,544,661
[45] Date of Patent: Oct. 1, 1985

[54] FUNGICIDAL N-PYRIDYLOXY ALKYL AMINES

[75] Inventor: David C. K. Chan, Petaluma, Calif.

[73] Assignee: Chevron Research Company, San Francisco, Calif.

[21] Appl. No.: 535,176

[22] Filed: Sep. 23, 1983

[51] Int. Cl.⁴ .................. C07D 213/64; C07D 213/65; A01N 43/40
[52] U.S. Cl. ..................................... 514/345; 546/176; 546/261; 546/276; 546/278; 546/281; 546/300; 544/182; 544/224; 544/335
[58] Field of Search .......................... 546/300; 424/263

[56] References Cited

U.S. PATENT DOCUMENTS 4,391,629  7/1983  Aya et al. ................................ 71/94

*Primary Examiner*—Alan L. Rotman
*Attorney, Agent, or Firm*—D. A. Newell; T. G. DeJonghe; S. L. Biggs

[57] ABSTRACT

Compounds of the formula:

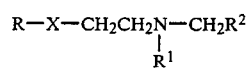

wherein
  X is oxygen or sulfur;
  R is pyridyl optionally substituted with 1 to 3 substituents independently selected from halogen, lower alkyl or lower alkoxy optionally substituted with 1 to 3 of the same or different halogen atoms or nitro, $R^1$ is lower alkyl; and $R^2$ is a 5- or 6-membered heterocyclic ring containing 1- to 3-ring nitrogens and the remainder of the ring atoms carbon atoms, a quinoline ring or a phenyl ring, all optionally substituted with 1 to 3 substituents independently selected from halogen, trihalomethyl, lower alkyl or lower alkoxy, provided that $R^2$ is not bonded to the —$CH_2$— group by a ring nitrogen and compatible salts thereof, are fungicidal.

20 Claims, No Drawings

FUNGICIDAL N-PYRIDYLOXY ALKYL AMINES

BACKGROUND OF THE INVENTION

This invention is drawn to novel fungicides.

With the world more dependent for food on an ever decreasing amount of cultivated farmland, it is increasingly important to develop effective fungicides which protect crops from fungicidal destruction.

Kozlik et al, in CA 79:533272Z disclosed 1-carbamoylimidazoles as insecticidal.

Brookes et al, in U.S. Pat. Nos. 4,080,462 and 3,991,071, disclosed 1-(N,N-disubstituted carbamoyl and thiocarbamoyl)-imidazoles as fungicidal.

Fungicidal compounds which are intermediates in the preparation of the compounds of this invention are disclosed in my concurrently filed and commonly-assigned U.S. patent application "Substituted heteroaryl Fungicides".

Commonly-assigned U.S. patent application, "Substituted Heteroaryl and Heteroaralkyl Amine Fungicides", Ser. No. 470,824, filed Feb. 28, 1983 discloses compounds of the formula:

$$R-X-CH_2CH_2-N(R^1)-CH_2R^2$$

wherein X is sulfur or oxygen; R is phenyl or phenyl substituted with 1 to 3 substituents independently selected from fluoro, chloro, bromo, iodo, lower alkyl or trihalomethyl; $R^1$ is lower alkyl or lower alkoxyalkyl; and $R^2$ is a 5- or 6-member heterocyclic ring having 1 to 3 ring nitrogens and the remainder of the ring atoms carbon atoms, optionally substituted with 1 to 2 independent lower alkyl groups, provided that a nitrogen of the 5- or 6-member heterocyclic ring is not bonded to the adjacent $-CH_2-$ group, or the group $-CH_2R^3$ where $R^3$ is a 5- or 6-member heterocyclic ring having 1- to 3-ring nitrogens and the remainder of the ring atoms carbon atoms.

SUMMARY OF THE INVENTION

The compounds of the present invention are represented by the formula:

$$R-X-CH_2CH_2-N(R^1)-CH_2R^2$$

wherein X is oxygen or sulfur; R is pyridyl optionally substituted with 1 to 3 substituents independently selected from halogen, lower alkyl or lower alkoxy optionally substituted with 1 to 3 of the same or different halogen atoms or nitro; $R^1$ is lower alkyl; and $R^2$ is a 5- or 6-membered heterocyclic ring containing 1 to 3 ring nitrogens and the remainder of the ring atoms carbon atoms, a quinoline ring or a phenyl ring, all optionally substituted with 1 to 3 substituents independently selected from halogen, trihalomethyl, lower alkyl or lower alkoxy, provided that $R^2$ is not bonded to the $-CH_2-$ group by a ring nitrogen, and compatible salts thereof.

Among other factors, the present invention is based upon my finding that the compounds of this invention are effective fungicides. In particular, some of the compounds of this invention possess good activity against certain plant fungal diseases such as Bean Powdery Mildew and Tomato Early Blight.

In part due to their superior fungicidal activity, preferred R groups include the trihalopyridyl group. Particularly preferred is the 3,5,6-trihalopyridyl group.

Preferred halogens include bromo and chloro.

Preferred $R^1$ groups include n-propyl and ethoxyethyl. Particularly preferred is n-propyl.

Preferred $R^2$ groups include, for instance, 3-pyridyl, 5-pyrimidyl, 2-pyrazyl, 5-(1-methylimidazolyl), 1-methyl-1,2,4-triazolyl, 3-picolyl, 2-methyl-pyrazyl, 2-iodophenyl, 2-trifluoromethylphenyl, and the like.

Definitions

As used herein, the following terms have the following meanings, unless expressly stated to the contrary.

The term "alkyl" refers to both straight- and branched-chain alkyl groups. Generally, such alkyl groups contain from 1 through 12 carbon atoms.

The term "lower alkyl" refers to both straight- and branched-chain alkyl groups having a total from 1 through 6 carbon atoms and includes primary, secondary and tertiary alkyl groups. Typical lower alkyls include, for example, methyl, ethyl, n-propyl, isopropyl, n-butyl, t-butyl, n-hexyl, and the like.

The term "halo" or "halogen atom" refers to the groups fluoro, chloro, bromo and iodo.

The term "alkoxy" refers to the group R'O— wherein R' is alkyl.

The term "lower alkoxy" refers to the alkoxy groups having from 1 through 6 carbon atoms and includes, for example, methoxy, ethoxy, t-butoxy, hexoxy, and the like.

The term "alkylene" refers to the group $-(CH_2)_z-$, where z is an integer greater than zero.

The term "lower alkylene" refers to alkylene groups having from 1 to 6 carbon atoms and includes, for example, methylene, ethylene, propylene, and the like.

The term "haloalkyl" refers to alkyl groups having one or more halo substituents. Typical haloalkyl groups include, for example, trifluoromethyl, dichloromethyl, bromochloromethyl, 1,2-dibromoethyl, 3-iodopropyl, chloromethyl, and the like.

The term "compatible salts" refers to those salts that do not appreciably adversely affect the biological activity of the fungicidal compound in question and includes, for example, the hydrochloride salts of such compounds.

The term "a 6-member heterocyclic ring containing 1 to 3 ring nitrogens" refers to groups such as pyridyl, pyridazinyl, pyrimidyl, pyrazyl, triazinyl, and the like.

The term "a 5-member heterocyclic ring containing 1 to 3 nitrogen atoms" refers to the groups such as imidazolyl, pyrrolyl, pyrazolyl, triazolyl, and the like.

The term "ethanolamine" refers to the group $HOCH_2CH_2NH_2$.

The term "N-(3-pyridylcarbonyl)ethanolamine" refers to the group:

$$HOCH_2CH_2\overset{H}{N}\overset{O}{\overset{\|}{C}}-\text{(3-pyridyl)}$$

The term "2-aminoethanethiol" refers to the group $HSCH_2CH_2NH_2$.

The term "N-(3-pyridylcarbonyl), N-(n-propyl) 2-aminoethanethiol" refers to the group:

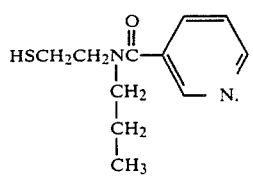

The term "a heterocycle containing a free nitrogen" refers to those heterocycles in which the nitrogen of the heterocycle is bonded with a hydrogen and includes, for instance, pyrrole

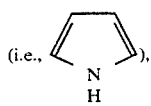

1,2,4-triazole

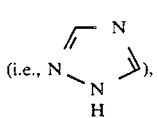

imidazole

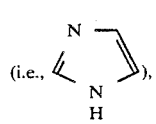

pyrazole

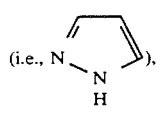

and the like.

The term "heteroaralkyl" refers to a lower alkyl group substituted with a 5- or 6-member heterocyclic ring containing 1 to 3 nitrogen atoms, and refers to the groups 1-methyl-1,2,4-triazolyl, 3-picolyl, and the like.

The term "ethylenediamine" refers to the group $H_2NCH_2CH_2NH_2$.

The term "nicotine amide" refers to the group:

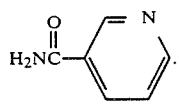

The term "pyrazinamide" refers to the group:

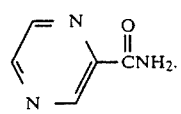

DETAILED DESCRIPTION OF THE INVENTION

The compounds of the present invention are conveniently prepared according to the following synthetic scheme:

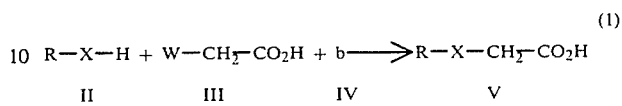

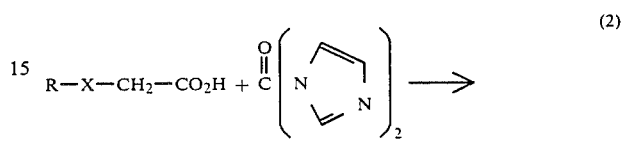

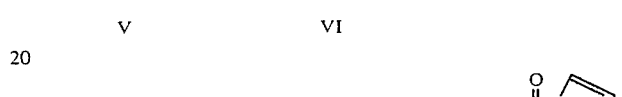

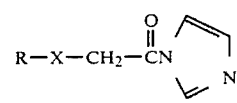

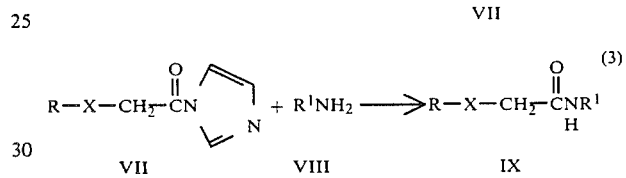

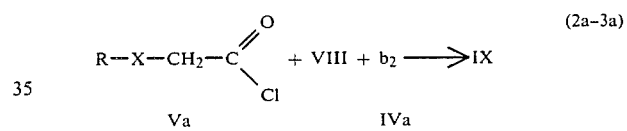

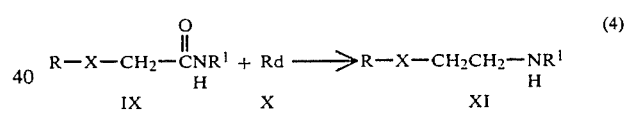

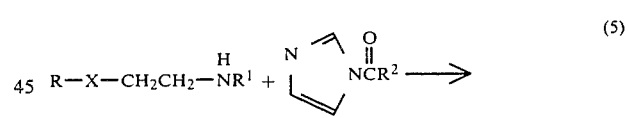

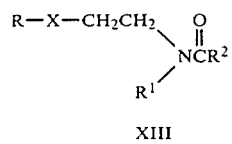

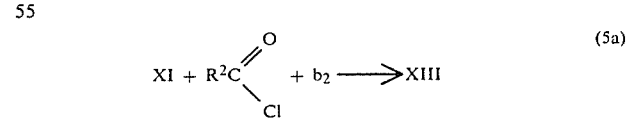

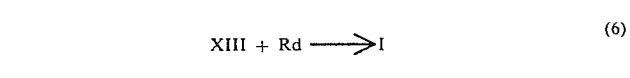

wherein R, $R^1$, $R^2$ and X are as defined above; W is a halogen, b is a base, $b_2$ is an acid scavenger (a base) and Rd is a reducing agent.

Reaction (1) is conducted by adding approximately 2 equivalents of a base, IV, to II. The reaction is done in the liquid phase employing an organic solvent such as ethanol, methanol, and the like, or, alternatively, water. Preferably, the base employed is an inorganic base. Suitable inorganic bases include, for instance, sodium hydride, sodium methoxide, metallic sodium, and the like. After addition of IV, an approximately equimolar amount of III, is added to the system. Reaction pressure is not critical and for convenience, the reaction is generally conducted at atmospheric pressure. The reaction is generally conducted at from 0° C. to 100° C., although preferably at from 40° C. to 70° C., and is generally complete from within 1 to 48 hours. The resulting intermediate, V, is isolated by conventional procedures such as extraction, filtration, chromatography, distillation, or alternatively, used in Reaction (2) without purification and/or isolation.

Reaction (2) is conducted by adding an essentially equimolar amount of carbonyldiimidazole, VI, to V. The reaction is conducted in the liquid phase using an inert anhydrous organic solvent such as chloroform, methtylene chloride, dimethoxyethane, toluene, and the like. Reaction pressure is not critical and for convenience, the reaction is generally conducted at atmospheric pressure. The reaction is generally conducted at from 0° C. to 100° C., although preferably at room temperature, and is generally complete from within 1 to 24 hours. The resulting carboxylic acid imidazolide, VII, may be isolated by conventional procedures such as extraction, filtration, chromatography, distillation, and the like. Alternatively and preferably, the resulting intermediate is not isolated from the reaction solution but is used directly in Reaction (3).

Reaction (3) is conducted by adding an essentially equimolar amount of the appropriate primary amine, VIII, to VII. The reaction is conducted in the liquid phase using an inert anhydrous organic solvent such as chloroform, methylene chloride, dimethoxyethane, toluene, and the like. Preferably, the reaction solution is the same as was employed in Reaction (2) with the appropriate amine, VIII, merely added to the system after completion of Reaction (2). Reaction pressure is not critical and for convenience, the reaction is generally conducted at atmospheric pressure. The reaction is generally conducted at from 0° C. to 100° C., although preferably at room temperature, and is generally complete from within 1 to 24 hours. The resulting amide, IX, is isolated by conventional procedures such as extraction, filtration, chromatography, distillation, or alternatively, used in Reaction (4) without purification and/or isolation.

Alternatively, IX may be prepared according to Reaction (2a-3a) by adding a solution of the acid chloride corresponding to V to a solution of VIII. The acid chloride Va is prepared from the acid V by techniques known to the art, such as treatment with thionyl chloride. The reaction is conducted in the presence of $b_2$ (IVa), an acid scavenger such as triethylamine, pyridine, an alkylamine, sodium carbonate, or the like. The reaction is conducted in the liquid phase using an inert organic solvent such as methylene chloride, chloroform, dioxane, toluene, and the like. The reaction is carried out at a temperature of about −50° C. to about 100° C., preferably from about 0° C. to about 25° C. After the addition is complete, the reaction mixture is allowed to return to room temperature. The reaction is generally complete within about 1 to about 48 hours after the addition is complete. The resulting amide IX is isolated by conventional procedures such as extraction, filtration, chromatography, distillation, or alternatively used in Reaction (4) without further purification or isolation.

Reaction (4) is a conventional reduction of the amide to the amine. In preparing compounds of this invention, the carbonyl of the amide is reduced to the methylene group; the reaction is conveniently conducted by adding an essentially equimolar amount of a reducing agent, Rd, to IX. The reaction is conducted in the liquid phase employing an inert anhydrous organic solvent such as toluene, benzene, and the like. Suitable reducing agents include, for instance, lithium aluminum hydride, borane, borane-methyl sulfide, and the like. Preferably, due to the ease in handling the reagent, borane-methyl sulfide is employed as the reducing agent. Reaction pressure is not critical and for convenience, the reaction is conducted at atmospheric pressure. The reaction is generally conducted at from 0° C. to 110° C., although preferably at from 30° C. to 70° C., and is generally complete from within 1 to 24 hours. The resulting amine, XI, is isolated by conventional procedures such as extraction, filtration, chromatography, distillation, or alternatively, used in Reaction (5) without purification and/or isolation.

Reaction (5) is conducted by first preparing reagent XII. XII is prepared by adding an essentially equimolar amount of carbonyldiimidazole to the appropriate acid, $R^2CO_2H$ wherein $R^2$ is as defined above. The reaction is conducted in the liquid phase using an inert anhydrous organic solvent such as chloroform, methylene chloride, dimethoxyethane, toluene, and the like. Reaction pressure is not critical and for convenience, the reaction is generally conducted at atmospheric pressure. The reaction is generally conducted at from 0° C. to 100° C., although preferably at room temperature, and is generally complete from within 1 to 24 hours. The resulting reagent, XII, may be isolated by conventional procedures such as extraction, filtration, chromatography, distillation, and the like. Alternatively and preferably, the reagent is not isolated from the reaction solution but an essentially equimolar amount of the amine, XI, is added to the system. Reaction pressure for this reaction is not critical and for convenience, the reaction is generally conducted at atmospheric pressure. After addition of XI, the reaction is generally conducted at room temperature and is generally complete from within 1 to 24 hours. The product, XIII, is then isolated by conventional procedures such as extraction, filtration, chromatography, and distillation, or alternatively, used in Reaction (6) without purification and/or isolation.

The compounds of Formula XIII are also fungicidal; they and their use as fungicides are disclosed in my commonly-assigned and concurrently-filed U.S. patent application, "Fungicidal N-Pyridyloxyalkyl Amides".

Alternatively, XIII may be prepared by Reaction (5a) using the acid chloride XIV corresponding to $R^2CO_2H$. Acid chloride XIV may be conveniently prepared by combining approximately equimolar amounts of $R^2CO_2H$ and thionyl chloride. The reaction is conducted in the liquid phase using an inert organic solvent such as methylene chloride, toluene, chloroform, and the like. It is preferred to conduct the reaction in the presence of a catalytic amount of dimethylformamide. The reaction mixture is heated to reflux and refluxed for about 1 to about 24 hours. The mixture is stirred until gas evolution ceases. After the temperature of the mixture returns to room temperature, XIV may be used in Reaction (5a) without purification or isolation. Since XIV is susceptible to hydrolysis, minimal handling of it is preferred.

Reaction (5a) is conducted by combining XIV, with XI and IVa. The reaction is conducted in the liquid phase using an inert organic solvent such as methylene chloride, chloroform, toluene and the like. Suitable acid scavengers, $b_2$ (IVa), include bases such as triethylamine, pyridine, an alkylamine, sodium carbonate, and the like. The reaction is carried out at a temperature of about $-25°$ C. to about 100° C., preferably from about 0° C. to about 25° C., and may be conveniently carried out at room temperature. The reaction is generally complete within about 1 to about 24 hours. Product XIII is then isolated by conventional procedures such as extraction, filtration, chromatography, distillation, or alternatively, used in Reaction (6) without purification and/or isolation.

Reaction (6) is a conventional reduction of the amide to the amine. In preparing the compounds of this invention, the carbonyl of the amide XIII is reduced to a methylene group. The reaction is conveniently conducted by adding an essentially equimolar amount of a reducing agent, Rd, to XIII. The reaction is conducted in the liquid phase employing an inert anhydrous organic solvent such as toluene, benzene and the like. Preferably, due to the ease in handling the reagent, borane-methyl sulfide is employed as the reducing agent. Reaction pressure is not critical and, for convenience, the reaction is conducted at atmospheric pressure. The reaction is generally conducted at from about 25° C. to about 110° C., although preferably at from about 50° C. to about 75° C. and is generally complete within from about 2 to about 18 hours. The resulting product, I, is isolated by conventional procedures such as extraction, filtration, chromatography, distillation or the like.

Utility

The compounds of the invention are effective in controlling fungal infections. Some of the compounds of this invention are particularly effective in controlling powdery mildew fungal infections caused by the organism *Erysiphe polygoni*. Some of the compounds of this invention are also useful for controlling leaf blights caused by organisms such as *Phytophthora infestans conidia, Alternaria solani conidia,* and *Septoria apii*. Some of the compounds of this invention are also useful for controlling fungal infections caused by *Uromyces phaseoli tipica, Plasmopara viticola,* and *Piricularia oryzae*. However, some fungicidal compounds of this invention may be more fungicidally active than others against particular fungi.

When used as fungicides, the compounds of the invention are applied in fungicidally effective amounts to fungi and/or their habitats, such as vegetative hosts and non-vegetative hosts, e.g., animal products. The amount used will, of course, depend on several factors such as the host, the type of fungus, and the particular compound of the invention. As with most pesticidal compounds, the fungicides of the invention are not usually applied full strength, but are generally incorporated with conventional, biologically inert extenders or carriers normally employed for facilitating dispersion of active fungicidal compounds, recognizing that the formulation and mode of application may affect the activity of the fungicide. Thus, the fungicides of the invention may be formulated and applied as granules, as powdery dusts, as wettable powders, as emulsifiable concentrates, as solutions, or as any of several other known types of formulations, depending on the desired mode of application.

Wettable powders are in the form of finely divided particles which disperse readily in water or other dispersants. These compositions normally contain from about 5% to 80% fungicide, and the rest inert material, which includes dispersing agents, emulsifying agents and wetting agents. The powder may be applied to the soil as a dry dust, or preferably as a suspension in water. Typical carriers include fuller's earth, kaolin clays, silicas, and other highly absorbent, readily wettable, inorganic diluents. Typical wetting, dispersing or emulsifying agents include, for example: the aryl and alkylaryl sulfonates and their sodium salts; alkylamide sulfonates, including fatty methyl taurides; alkylaryl polyether alcohols, sulfated higher alcohols and polyvinyl alcohols; polyethylene oxides; sulfonated animal and vegetable oils; sulfonated petroleum oils; fatty acid esters of polyhydric alcohols and the ethylene oxide addition products of such esters; and the addition products of long-chain mercaptans and ethylene oxide. Many other types of useful surface-active agents are available in commerce. The surface-active agent, when used, normally comprises from 1% to 15% by weight of the fungicidal composition.

Dusts are freely flowing admixtures of the active fungicide with finely divided solids such as talc, natural clays, kieselguhr, pyrophyllite, chalk, diatomaceous earths, calcium phosphates, calcium and magnesium carbonates, sulfur, lime, flours, and other organic and inorganic solids which act as dispersants and carriers for the toxicant. These finely divided solids have an average particle size of less than about 50 microns. A typical dust formulation useful herein contains 75% silica and 25% of toxicant.

Useful liquid concentrates include the emulsifiable concentrates, which are homogeneous liquid or paste compositions which are readily dispersed in water or other dispersant, and may consist entirely of the fungicide with a liquid or solid emulsifying agent, or may also contain a liquid carrier such as xylene, heavy aromatic naphthas, isophorone, and other nonvolatile organic solvents. For application, these concentrates are dispersed in water or other liquid carrier, and are normally applied as a spray to the area to be treated.

Other useful formulations for fungicidal applications include simple solutions of the active fungicide in a dispersant in which it is completely soluble at the desired concentration, such as acetone, alkylated naphthalenes, xylene, or other organic solvents. Granular formulations, wherein the fungicide is carried on relatively coarse particles, are of particular utility for aerial distribution or for penetration of cover-crop canopy. Pressurized sprays, typically aerosols wherein the active ingredient is dispersed in finely divided form as a result of vaporization of a low-boiling dispersant solvent carrier, such as the Freons, may also be used. All of those techniques for formulating and applying fungicides are well known in the art.

The percentages by weight of the fungicide may vary according to the manner in which the composition is to be applied and the particular type of formulation, but in general comprise 0.5% to 95% of the toxicant by weight of the fungicidal composition.

The fungicidal compositions may be formulated and applied with other active ingredients, including other fungicides, insecticides, nematocides, bactericides, plant-growth regulators, fertilizers, etc.

A further understanding of the invention can be had in the following non-limiting Examples. Wherein, unless expressly stated to the contrary, all temperature ranges refer to the Centigrade system and the term "ambient" or "room temperature" refers to about 20° C. to 25° C. The term "percent" refers to gram moles. The term "equivalent" refers to a quantity of reagent equal in moles, to the moles of the preceding or succeeding reagent recited in that example in terms of finite moles or finite weight or volume. Also, unless expressly stated to the contrary, geometric isomer and racemic mixtures are used as starting materials and correspondingly, isomer mixtures are obtained as products.

EXAMPLES

EXAMPLE 1

Preparation of

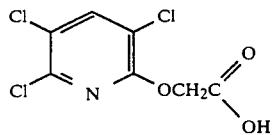

3,5,6-Trichloro-2-pyridyloxyacetic Acid

To a mixture of a 50-ml solution of the triethylamine salt of 3,5,6-trichloro-2-pyridyloxyacetic acid (Garlon 3A) and 200 ml methylene chloride, 30 ml concentrated hydrochloric acid were added with stirring. Gradually, a precipitate separated from the lower organic layer. Methylene chloride (100 ml) and ethyl ether (100 ml) were added to give two clear layers. The lower combined organic layer was separated, dried over magnesium sulfate, and then filtered. The filtrate was stripped in vacuo to give 20.1 g of the above-identified product as a tan solid.

EXAMPLE 1A

Preparation of 3,5,6-trichloro-2-pyridyloxyacetic Acid

To 450 ml of a stirred solution of Garlon 3A (triethylamine salt of 3,5,6-trichloro-2-pyridyloxyacetic acid), 250 ml concentrated hydrochloric acid was added with stirring. A precipitate formed. The mixture was diluted to 1500 ml with water. The precipitate was filtered, washed with water, pressed dried and then dried inside the hood to give 176 g of the above-identified product as a beige solid.

EXAMPLE 2

Preparation of

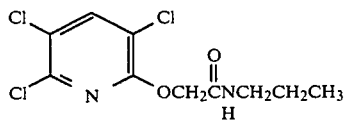

N-(n-propyl)-3,5,6-trichloropyridyloxyacetamide (a) To a stirred slurry of 30 g (0.1237 mole) 3,5,6-trichloro-2-pyridyloxyacetic acid in 500 ml methylene chloride, 1 ml N,N-dimethylformamide was added. Then 16.2 g [10 m' (0.136 mole)] thionyl chloride was added dropwise. The mixture was refluxed 3½ hours. The solvent was stripped in vacuo to give the 3,5,6-trichloro-2-pyridyloxyacetyl chloride as an oil, which was used in step (b) without further isolation.

(b) The 3,5,6-trichloro-2-pyridyloxyacetyl chloride from step (a) in 100 ml methylene chloride was added over a period of one hour to a stirred solution of 23 ml n-propylamine in 425 ml methylene chloride (maintained at ice water temperature) in an ice water bath. The reaction mixture was stirred overnight at ambient temperature. The reaction mixture was washed twice with water (250 ml), dried over magnesium sulfate and then stripped. The filtrate was stripped in vacuo to give a residue. The residue was slurried with petroleum ether and filtered to give 35.1 g of the above-identified acid amide as a white solid.

EXAMPLE 3

Preparation of

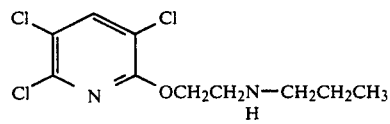

N-(n-propyl)ethanolamine 3,5,6-trichloropyridylether

To a stirred solution of 36.8 g (0.124 mole) N-(n-propyl)-3,5,6-trichloropyridyloxyacetamide (Example 2) in 300 ml tetrahydrofuran at room temperature, 27.2 ml 10.272 mole)boranemethyl sulfide were added in three portions (9 ml, 9 ml and 9.2 ml) rapidly through a syringe. The reaction mixture was stirred at its own exotherm, and then at ambient temperature under nitrogen gas overnight. The gel-like mixture was then refluxed under nitrogen gas for two hours. The stirred reaction mixture was then placed in an ice water bath while 60 ml methanol was added dropwise over ½ hour resulting in gas ($H_2$) evolution to give a clear solution. The solution was stirred until bubbling (gas evolution) ceased. The reaction mixture was stripped in vacuo to give an oil. The oil was dissolved in 325 ml methylene chloride. To that stirred mixture in an ice bath, 36 ml concentrated hydrochloric acid were added dropwise over ½ hour. The resulting mixture was stirred at ambient temperature until gas evolution ceased (about 5 hours). Water (250 ml) was added to the reaction mixture; then concentrated sodium hydroxide (50%) was added until the pH of the mixture reached 10 (about 25 ml). Additional water (200 ml) and methylene chloride (200 ml) were added to the reaction mixture. The resulting mixture was stirred until there were 2 clear layers. The organic layer was separated, washed with water (about 250 ml), dried over magnesium sulfate and filtered. The filtrate was stripped in vacuo to give an oily residue. The residue was slurried in petroleum ether. The petroleum ether mixture was filtered (to remove solids). The filtrate was stripped in vacuo to give 30.3 g of the above-identified product as an oil.

EXAMPLE 4

Preparation of

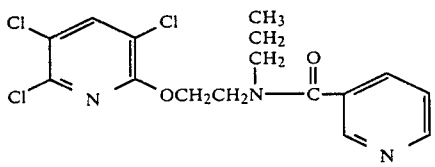

N-(n-propyl), N-(3-pyridylcarbonyl)ethanolamine 3,5,6-trichloropyridylether (a) A slurry of 1.8 g (0.015 mole)nicotinic acid and 2.4 g (0.015 mole) 1,1'-carbonyl diimidazole in 75 ml methylene chloride was heated at reflux for two hours to form the 3-pyridine carboxylic acid imidazolide.

(b) Then 3.3 g (0.0116 mole) N-(n-propyl)ethanolamine 3,5,6-trichloropyridylether in 10 ml methylene chloride was added to the imidazolide solution from step (a). The reaction mixture was refluxed a total of 65¾ hours. The reaction mixture was washed with water (50 ml), then with a saturated sodium bicarbonate solution (50 ml), dried over magnesium sulfate, and then filtered. The filtrate was stripped in vacuo to give 4.7 g of an oil.

The oil was dissolved in about 10 ml methylene chloride and chromatographed on a (300 g) silica gel column, eluting sequentially with petroleum ether (1 liter), 70% petroleum ether/ethyl ether (1liter), 60% petroleum ether/ethyl ether (1liter), 50% petroleum ether/ethyl ether (1 liter), 25% petroleum ether/ethyl ether (1 liter), 10% petroleum ether/ethyl ether (1 liter), and ethyl ether (2liters) to give an oil. The oil was combined with ethyl ether (about 100 ml), washed with a saturated sodium bicarbonate solution (50 ml), dried over mangesium sulfate and filtred. The filtrate was stripped in vacuo to give 1.8 g of the above-identified product as a yellow oil.

Elemental analysis for $C_{16}H_{16}Cl_3N_3O_2$ showed: calculated %C 49.44, %H 4.15, and %N 10.81; found %C 49.51, %H 4.46 and %N 11.82.

Further elution of the above column with 80/20 ethylether/methanol gave an oil. The oil was dissolved in ethyl ether (about 250 ml), dried over magnesium sulfate and filtered. The filtrate was stripped in vacuo to give 2.2 g of an oil which IR and NMR spectra identified as the above-identified product. Thus, the combined yield was 4.0 g.

EXAMPLE 5

Preparation of

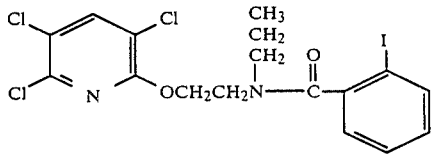

N-(n-propyl), N-(2-iodobenzoyl ethanolamine 3,5,6-trichloropyridylether (a) To a stirred slurry of 5.0 g (0.02 mole) O-iodobenzoic acid in 100 ml methylene chloride, 2.6 g [1.6 ml (0.022 mole)] thionyl chloride were added quickly. Two drops N,N-dimethylformamide were then added to the reaction mixture. The reaction mixture was refluxed for 16 hours. Additional thionyl chloride (2.6 g) was added and the resulting mixture was refluxed 5 more hours. The solvent was stripped to give the O-iodobenzoyl chloride which was used in step (b) without further isolation.

(b) To a stirred solution of 5.7 g (0.020 mole) N-(n-propyl)ethanolamine 3,5,6-trichloropyridylether (Example 3) and 2.2 g (0.022 mole)triethylamine in 100 ml methylene chloride a solution of the acid chloride from step (a) in 15 ml methylene chloride was added slowly. The reaction mixture was stirred overnight at ambient temperature. Water (100 ml) was added to the reaction mixture. The organic layer was separated, washed with 50 ml of a saturated sodium bicarbonate solution, dried over magnesium sulfate, and then filtered. The filtrate was stripped in vacuo to give an oil. The oil was chromatographed on silica gel (260 g) eluting sequentially with petroleum ether (1 liter), 80% petroleum ether in ethyl ether (1 liter), and 70% petroleum ether (3 liter) to give an oil. The fractions were combined in methylene chloride (about 250 ml) and then stripped in vacuo to give a viscous oil which crystallized on standing over the weekend. Trituration with ethyl ether/petroleum ether 5/95 gave 8.2 g the above-identified product as a crystalline white solid.

Elemental analysis for $C_{17}H_{16}Cl_3IN_2O_2$ showed: calculated %C 39.76, %H 3.14, and %N 5.45; found %C 39.49, %H 3.18, and %N 5.65.

EXAMPLE 6

Preparation of

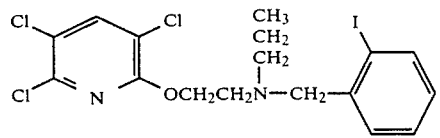

N-(n-propyl), N-(2-iodobenzyl)ethanolamine 3,5,6-trichloropyridylether

To a stirred solution of 4.5 g (0.00876 mole) N-(n-propyl), N-(2-iodobenzoyl)ethanolamine 3,5,6-trichloropyridylether and 100 ml tetrahydrofuran under nitrogen gas, 1.8 ml (0.0175 mole) borane-dimethyl sulfide were added. The reaction mixture was stirred overnight at ambient temperature under nitrogen gas. The reaction mixture was refluxed four hours. Methanol (5 ml) was added to the stirred reaction mixture. After evolution of gas ($H_2$) had subsided, the solvent was stripped in vacuo to give a viscous oil. The oil was dissolved in 100 ml methylene chloride and 15 ml concentrated hydrochloric acid was added; then the reaction mixture was stirred overnight at ambient temperature. Excess concentrated sodium hyddroxide (50%) was added dropwise (about 25 ml) to the reaction mixture, cooling the reaction mixture with an ice water bath during the addition. The reaction mixture was stirred at ambient temperature 21½ hours (overnight). The organic layer was separated, dried over magnesium sulfate and filtered. The filtrate was stripped in vacuo to give 5.3 g of crude product as an oil.

The oil was chromatographed on silica gel (175 g) eluting sequentially with: petroleum ether to give an oil, and then 95% petroleum ether in ethyl ether (1½ liter) to give an additional oil fraction. The oil fractions were combined in methylene chloride (about 250 ml). The methylene chloride solution was dried over magnesium sulfate and then filtered. The filtrate was stripped in vacuo to give 3.6 g of the above-identified product as an oil.

Elemental analysis for $C_{17}H_{18}Cl_3IN_2O$ showed: calculated %C 40.87, %H 3.63, and %N 5.61; found %C 41.94, %H 4.02, and %N 5.63.

EXAMPLE 7

Preparation of

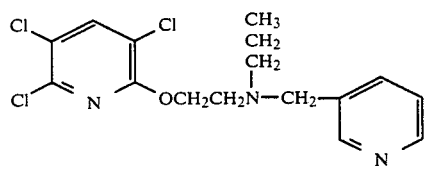

N-(n-propyl), N-(3-picolyl)ethanolamine 3,5,6-trichloropyridylether

To a stirred solution of 2.5 g (0.00643 mole) N-(n-propyl), N-(3-pyridylcarbonyl)ethanolamine 3,5,6-trichloropyridylether (the product of Example 5) in 50 ml tetrahydrofuran, 1.3 ml (0.013 mole)borane-dimethylsulfide was added through a syringe. The reaction mixture was stirred at ambient temperarture 1½ hours and then refluxed 3 hours. Additional tetrahydrofuran (20 ml) was added to the reaction mixture slurry and it was refluxed an additional 3 hours. After the reaction mixture was cooled to room temperature, 5 ml methanol was added to the slurry to give a clear solution. The solution was stripped in vacuo to give a viscous oil. The oil was dissolved in 100 ml methylene chloride; then 5 ml concentrated hydrochloric acid was added quickly. The reaction mixture was stirred at ambient temperature overnight. To the stirred mixture, 10 ml 10% sodium hydroxide was added dropwise, followed by 20 ml water, and an additional 6 ml 10% sodium hydroxide, giving a pH of 8.9. The lower organic layer was separated and washed with a brine solution (50 ml) to give a clear solution. The organic layer was dried over magnesium sulfate and then filtered. The filtrate was stirred in vacuo to give 2.2 g of crude product as an oil.

The oil was chromatographed on silica gel (120 g) eluting sequentially with (a) petroleum ether (1 l), (b) 90% petroleum ether in ethyl ether (1 liter), (c) 75% petroleum ether in ethyl ether (1 liter) giving an oil; and (d) 50% petroleum ether in ethyl ether (1½ liter) giving a white oil. The oil fractions [(c) and (d)] were combined in ethyl ether (about 200 ml). The ethereal solution was dried over magnesium sulfate and filtered. The filtrate was stripped in vacuo to give 1.7 g of the above-identified product as an oil.

Elemental analysis for $C_{16}H_{18}Cl_3N_O$ showed: calculated %C 51.29, %H 4.84 and %N 11.21; found %C 51.26, %H 5.02, and %N 11.51.

Compounds made in accordance with Examples 1 to 7 are shown in Table I.

EXAMPLE A

Bean Powdery Mildew

The compounds of the invention were tested for the control of the Bean Powdery Mildew organism *Erysiphe polygoni*. Seedling bean plants were sprayed with a 250-ppm solution of the test compound in acetone, water and a nonionic emulsifier. The sprayed plants were then inoculated 1 day later with the organism. The plants were maintained for 10 days at temperatures of 68° F. at night with daytime temperatures of 72° F. to 80° F.; relative humidity was maintained at 40% to 60%. The percent disease control provided by a given test compound was based on the percent disease reduction relative to the untreated check plants. The results are tabulated in Table II.

EXAMPLE B

Tomato Late Blight

Compounds of the invention were tested for the preventative control of the Tomato Late Blight organism *Phytophthora infestans*. Five- to six-week-old tomato (cultivar Bonny Best) seedlings were used. The tomato plants were sprayed with a 250-ppm suspension of the test compound in acetone, water and a nonionic emulsifier. The sprayed plants were then inoculated 1 day later with the organism, placed in an environmental chamber and incubated at 66° F. to 68° F. and 100% relative humidity for at least 16 hours. Following the incubation, the plants were maintained in a greenhouse for approximately 7 days. The percent disease control provided by a given test compound was based on the percent disease reduction relative to untreated check plants. The results are tabulated in Table II.

EXAMPLE C

Celery Late Blight

The Celery Late Blight tests were conducted using celery (Utah) plants 11 weeks old. The Celery Late Blight organism was *Septoria apii*. The celery plants were sprayed with 250-ppm solutions of the candidate toxicant mixed with acetone, water and a nonionic emulsifier. The plants were then inoculated with the organism and placed in an environmental chamber and incubated at 66° F. to 68° F. in 100% relative humidity for an extended period of time (approximately 48 hours). Following the incubation, the plants were allowed to dry and then were maintained in a greenhouse for approximately 14 days. The percent disease control provided by a given candidate toxicant is based on the percent disease reduction relative to untreated check plants. The results are reported in Table II.

EXAMPLE D

Tomato Early Blight

Compounds of the invention were tested for the control of the Tomato Early Blight organism *Alternaria solani conidia*. Tomato (variety Bonny Best) seedlings of 6- to 7-weeks old were used. The tomato plants were sprayed with a 250-ppm solution of the test compound in an acetone-and-water solution containing a small amount of a nonionic emulsifier. The sprayed plants were inoculated 1 day later with the organism, placed in the environmental chamber and incubated at 66° F. to 68° F. and 100% relative humidity for 24 hours. Following the incubation, the plants were maintained in a greenhouse for about 12 days. Percent disease control was based on the percent disease development on untreated check plants. The compounds tested and the results are tabulated in Table II.

EXAMPLE E

Grape Downy Mildew

The compounds of this invention were tested for the control of the Grape Downy Mildew organism, *Plas-*

*mopara viticola.* Seedlings of *Vitis vinifera* var. Emperor (7+ weeks old) were used as hosts. The plants were sprayed with a 250 ppm solution of the test compound in an acetone and water solution containing a small amount of non-ionic emulsifier. The treated plants were inoculated one day later by spraying them with a sore suspension of the organism. The treated plants were then held in a greenhouse at a temperature of about 68° F. to about 72° F. (relative humidity varied between about 30 and about 99%) for 4 days. The plants were then placed in an environmental chamber at 100% relative humidity to induce sporulation. On removal from the chamber and after drying, the plants were evaluated for disease development. The percent disease control provided by a given test compound was based on the percent disease reduction relative to untreated check plants. The results are reported in Table II.

EXAMPLE F

Leaf Rust

The Leaf Rust test was made using pinto beans. The pathogen was *Uromyces phaseoli tipica.* The pinto bean plants were sprayed with a 250-ppm solution of the test compound in an acetone-water mixture containing a nonionic emulsifier. The treated plants were inoculated thereafter with the pathogen and then incubated in an environmental chamber for approximately 20 hours at 100% relative humidity and a temperature of 68° F. to 70° F. The plants were then removed from the chamber, allowed to dry, and then maintained in a greenhouse at a 60% to 80% relative humidity. The rate of infection on the leaves was made after about 14 days. The percent disease control provided by a given test compound was based on the percent disease reduction relative to untreated check plants. The results are reported in Table II.

EXAMPLE G

Rice Blast

Compounds of this invention were tested for control of the Rice Blast organism *Piricularia oryzae,* using 10- to 14-day-old rice plant seedlings (Calrose M-9 variety). Seedling plants were sprayed with a 625-ppm solution of the test compound in acetone, water and a nonionic emulsifier (ORTHO X-77 spreader). The sprayed plants were inoculated 1 day later with the organism in an environmental chamber. After inoculation, the plants were kept in an environmental chamber for about 48 hours under conditions of about 72° F. to 75° F. and about 100% relative humidity. Following the incubation period, the plants were placed in a greenhouse with a temperature of about 72° F. and maintained with bottom watering for about 12 to 16 days. The percent disease control provided by a given test compound is based on a comparison of the percentage disease relative to the percent disease development on the untreated check plants:

$$\% \text{ Control} = 100 - 100 \times \left( \frac{\% \text{ disease in treated plants}}{\% \text{ disease in check}} \right)$$

The results are tabulated in Table II.

EXAMPLE H

Mycelial Inhibition

A number of the compounds of the present invention were evaluated for in vitro fungicidal effectiveness by means of a mycelial inhibition test. This test is designed to measure the fungitoxic activity of fungicidal chemicals in terms of their degree of inhibition of mycelium growth. Fungi used were *Phythium ultimum, Rhizoctonia solani, Fusarium monilofroma, Botrytis cinerea* and *Aspargillos niger.* Each compound to be tested was dissolved in acetone to 500 ppm concentration. Paper strips were infused with the particular mycelium growth by covering the paper with a potato dextrose broth culture of mycelial suspension. The papers were then placed on potato dextrose agar plates and sprayed by means of a microsprayer with the fungicidal solution. The treated paper strips were incubated at 25° C. and the data is taken after 24 hours. Fungicidal activities are measured by a zone of inhibited mycelial growth from the center of the paper strip in terms of mg/cm² needed for 99% control of the fungus ($ED_{99}$). The effectiveness of the compounds tested for fungicidal activity is reported in Table II in terms of the percent of the $ED_{99}$ of the test compound of the $ED_{99}$ of the standard Difolatan ®.

TABLE I

Compounds of the formula:

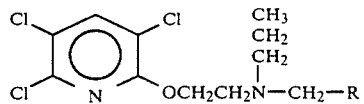

| Compound No. | R | Physical State | ELEMENTAL ANALYSIS | | | | | |
|---|---|---|---|---|---|---|---|---|
| | | | % Carbon | | % Hydrogen | | % Nitrogen | |
| | | | Calc. | Found | Calc. | Found | Calc. | Found |
| 1 42317 | (pyridyl) | yellow oil | 51.29 | 51.26 | 4.84 | 5.02 | 11.21 | 11.51 |
| 2 42574 | (CF₃-phenyl).HCl | white solid, mp 139–140° C. | 45.21 | 45.63 | 4.01 | 4.21 | 5.86 | 5.94 |

TABLE I-continued

Compounds of the formula:

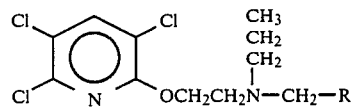

| Compound No. | R | Physical State | ELEMENTAL ANALYSIS | | | | | |
|---|---|---|---|---|---|---|---|---|
| | | | % Carbon | | % Hydrogen | | % Nitrogen | |
| | | | Calc. | Found | Calc. | Found | Calc. | Found |
| 3 42785 | 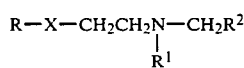 | milky oil | 40.87 | 41.94 | 3.63 | 4.02 | 5.61 | 5.63 |

TABLE II

| | FUNGICIDAL ACTIVITY | | | | | | |
|---|---|---|---|---|---|---|---|
| Compound No. | GDM | TLB | RB | TEB | CLB | BPM | BR |
| 1 42317 | 0 | 0 | 0 | 0 | 0 | 87 | 0 |
| 2 42574 | 0 | 0 | 0 | 0 | 50 | 100 | 0 |
| 3 42785 | — | 0 | 16 | 0 | 0 | 100 | 0 |

GDM - Grape Downy Mildew (*Plasmopara viticola*)
TLB - Tomato Late Blight (*Phytophthora infestans*)
CLB - Celery Late Blight (*Septoria apii*)
TEB - Tomato Early Blight (*Alternaria solani conidia*)
BR - Bean Rust (*Uromyces phaseoli tipica*)
BPM - Bean Powdery Mildew (*Erysiphe polygoni*)
RB - Rice Blast (*Piricularia oryzae*)

What is claimed is:

1. A compound of the formula:

$$R-X-CH_2CH_2N-CH_2R^2$$
$$\phantom{R-X-CH_2CH_2N}|$$
$$\phantom{R-X-CH_2CH_2N}R^1$$

wherein X is sulfur or oxygen; R is pyridyl optionally substituted with 1 to 3 substituents independently selected from halogen, lower alkyl or lower alkoxy optionally substituted with 1 to 3 of the same or different halogen atoms or nitro; $R^1$ is lower alkyl; and $R^2$ is phenyl or substituted phenyl substituted with 1 to 3 substituents independently selected from halogen trihalomethyl, lower alkyl or lower alkoxy, and compatible salts thereof.

2. A compound according to claim 1 wherein $R^2$ is phenyl optionally substituted with 1 to 3 substituents independently selected from halogen, trihalomethyl, lower alkyl or lower alkoxy.

3. A compound according to claim 1 wherein R is 3,5,6-trichloropyridyl.

4. A compound according to claim 3 wherein X is oxygen.

5. A compound according to claim 4 wherein $R^2$ is 2-trifluoromethylphenyl.

6. A compound according to claim 5 wherein $R^1$ is n-propyl.

7. A compound according to claim 4 wherein $R^2$ is 2-iodophenyl.

8. A compound according to claim 7 wherein $R^1$ is n-propyl.

9. A method of controlling fungi which comprises contacting said fungi or their growth environment with a fungicidally effective amount of a compound of claim 1.

10. A method of controlling fungi which comprises contacting said fungi or their growth environment with a fungicidally effective amont of a compound of claim 5.

11. A method of controlling fungi which comprises contacting said fungi or their growth environment with a fungicidally effective amount of a compound of claim 2.

12. A method of controlling fungi which comprises contacting said fungi or their growth environment with a fungicidally effective amount of a compound of claim 3.

13. A method of controlling fungi which comprises contacting said fungi or their growth environment with a fungicidally effective amount of a compound of claim 6.

14. A method of controlling fungi which comprises contacting said fungi or their growth environment with a fungicidally effective amount of a compound of claim 8.

15. A fungicidal composition which comprises an inert carrier and a fungicidally effective amount of a compound of claim 1.

16. A fungicidal composition which comprises an inert carrier and a fungicidally effective amount of a compound of claim 5.

17. A fungicidal composition which comprises an inert carrier and a fungicidally effective amount of a compound of claim 2.

18. A fungicidal composition which comprises an inert carrier and a fungicidally effective amount of a compound of claim 3.

19. A fungicidal composition which comprises an inert carrier and a fungicidally effective amount of a compound of claim 6.

20. A fungicidal composition which comprises an inert carrier and a fungicidally effective amount of a compound of claim 8.

* * * * *